United States Patent
Asogawa (10) Patent No.: US 11,385,168 B2
(45) Date of Patent: Jul. 12, 2022

(54) SPECTROSCOPIC ANALYSIS APPARATUS, SPECTROSCOPIC ANALYSIS METHOD, AND READABLE MEDIUM

(71) Applicant: NEC Corporation, Tokyo (JP)

(72) Inventor: Minoru Asogawa, Tokyo (JP)

(73) Assignee: NEC CORPORATION, Tokyo (JP)

( * ) Notice: Subject to any disclaimer, the term of this patent is extended or adjusted under 35 U.S.C. 154(b) by 123 days.

(21) Appl. No.: 15/562,053

(22) PCT Filed: Dec. 14, 2015

(86) PCT No.: PCT/JP2015/006225
§ 371 (c)(1),
(2) Date: Sep. 27, 2017

(87) PCT Pub. No.: WO2016/157270
PCT Pub. Date: Oct. 6, 2016

(65) Prior Publication Data
US 2018/0088029 A1     Mar. 29, 2018

(30) Foreign Application Priority Data

Mar. 31, 2015 (JP) .............................. JP2015-071618

(51) Int. Cl.
*G01N 21/25*     (2006.01)
*G01N 33/58*     (2006.01)
(Continued)

(52) U.S. Cl.
CPC .............. *G01N 21/25* (2013.01); *C12M 1/00* (2013.01); *C12Q 1/686* (2013.01); *C12Q 1/6825* (2013.01);
(Continued)

(58) Field of Classification Search
CPC ... G01N 2021/6441; G01N 2021/6439; G01N 21/6428; G01N 33/582; G01J 3/4406; G01J 3/44
See application file for complete search history.

(56) References Cited

U.S. PATENT DOCUMENTS 5,221,959 A * 6/1993 Ohyama .................... G01J 3/51
356/310
5,227,986 A * 7/1993 Yokota ...................... G01J 3/28
250/339.07
(Continued)

FOREIGN PATENT DOCUMENTS

JP     2005-095581 A     4/2005
JP     2005-274496 A     10/2005
(Continued)

OTHER PUBLICATIONS

International Search Report of PCT/JP2015/006225 dated Mar. 1, 2016.

*Primary Examiner* — Rufus L Phillips
(74) *Attorney, Agent, or Firm* — Sughrue Mion, PLLC (57) ABSTRACT

A spectroscopic analysis apparatus, a spectroscopic analysis method, and a program capable of appropriately analyzing a sample are provided. The spectroscopic analysis apparatus according to an embodiment includes: a light source (13) generates light to be incident on a sample including a plurality of substances labeled by a plurality of labeled substances; a spectrometer (14) disperse observed light generated in the sample by the light incident on the sample; a detector (15) detects the observed light dispersed by the spectrometer (14) to output observed spectral data; and a processor (16) analyzes the plurality of substances included in the sample based on the observed spectral data output from the detector (15), the processor (16) analyzing the substances included in the sample using a generalized (Continued)

inverse of a matrix having, as elements, reference spectral data set for the plurality of labeled substances and data of a noise component.

12 Claims, 4 Drawing Sheets

(51) Int. Cl.

| | |
|---|---|
| *G01N 21/64* | (2006.01) |
| *C12Q 1/686* | (2018.01) |
| *G01N 27/447* | (2006.01) |
| *C12Q 1/6825* | (2018.01) |
| *C12M 1/00* | (2006.01) |
| *G01J 3/443* | (2006.01) |
| *G01J 3/44* | (2006.01) |
| *G01J 3/28* | (2006.01) |

(52) U.S. Cl.
CPC . *G01J 3/28* (2013.01); *G01J 3/44* (2013.01); *G01J 3/443* (2013.01); *G01J 3/4406* (2013.01); *G01N 21/645* (2013.01); *G01N 21/6428* (2013.01); *G01N 33/582* (2013.01); *G01N 27/44721* (2013.01); *G01N 2021/6423* (2013.01); *G01N 2021/6439* (2013.01); *G01N 2201/121* (2013.01); *G01N 2201/126* (2013.01); *G01N 2201/1293* (2013.01)

(56) References Cited

U.S. PATENT DOCUMENTS

| | | | | |
|---|---|---|---|---|
| 5,710,876 A | * | 1/1998 | Peercy | G06T 15/506 |
| | | | | 345/426 |
| 5,863,403 A | * | 1/1999 | Middendorf | C12Q 1/6869 |
| | | | | 204/416 |
| 9,073,623 B1 | * | 7/2015 | Suh | G01M 11/083 |
| 2003/0020908 A1 | * | 1/2003 | Frost | G01J 3/10 |
| | | | | 356/317 |
| 2004/0126892 A1 | * | 7/2004 | Bogomolov | G01N 30/8624 |
| | | | | 436/161 |
| 2004/0267140 A1 | | 12/2004 | Ito et al. | |
| 2005/0243313 A1 | * | 11/2005 | Neher | G01N 21/6428 |
| | | | | 356/317 |
| 2009/0231421 A1 | | 9/2009 | Arai et al. | |
| 2010/0066874 A1 | * | 3/2010 | Ishiga | H04N 5/208 |
| | | | | 348/252 |
| 2010/0182510 A1 | * | 7/2010 | Gerkmann | G10L 21/0208 |
| | | | | 348/607 |
| 2011/0108711 A1 | * | 5/2011 | Tsupryk | G01N 21/645 |
| | | | | 250/214 R |
| 2011/0256631 A1 | * | 10/2011 | Tomaney | C12Q 1/6874 |
| | | | | 436/94 |
| 2012/0015825 A1 | * | 1/2012 | Zhong | G01N 21/6428 |
| | | | | 506/6 |
| 2013/0126618 A1 | * | 5/2013 | Gao | H04N 9/0451 |
| | | | | 235/469 |
| 2015/0039265 A1 | * | 2/2015 | Acharid | G01N 21/64 |
| | | | | 702/179 |
| 2015/0145978 A1 | | 5/2015 | Chiba | |
| 2015/0226608 A1 | | 8/2015 | Asogawa | |

FOREIGN PATENT DOCUMENTS

| | | |
|---|---|---|
| JP | 2008-051654 A | 3/2008 |
| JP | 2009-281933 A | 12/2009 |
| JP | 2013-240401 A | 12/2013 |
| WO | 2014/045481 A1 | 3/2014 |

* cited by examiner

$$b = A x \quad \cdots (5)$$

Fig. 4

$$r = b - A x \quad \cdots (6)$$

Fig. 5

$$A^T \quad A \; x = A^T A \; x = A^T b \quad \cdots (7)$$

SPECTROSCOPIC ANALYSIS APPARATUS, SPECTROSCOPIC ANALYSIS METHOD, AND READABLE MEDIUM

CROSS REFERENCE TO RELATED APPLICATIONS

This application is a National Stage of International Application No. PCT/JP2015/006225 filed Dec. 14, 2015, claiming priority based on Japanese Patent Application No. 2015-071618 filed Mar. 31, 2015, the contents of all of which are incorporated herein by reference in their entirety.

TECHNICAL FIELD

The present invention relates to a spectroscopic analysis apparatus, a spectroscopic analysis method, and a readable medium, and more particularly, to a spectroscopic analysis apparatus, a spectroscopic analysis method, and a readable medium that perform an analysis using spectra obtained by dispersing light generated in a sample.

BACKGROUND ART

Patent Literature 1 discloses a spectroscopic analysis apparatus in which DNA testing is performed using spectral data. In Patent Literature 1, a sample including DNA fragments labeled by fluorescent substances is irradiated with excitation light. By spectroscopically measuring the fluorescence generated in the sample, an observed spectrum is measured. By performing a matrix operation using a generalized inverse on spectral data, concentrations of the fluorescent substances are obtained.

CITATION LIST

Patent Literature

Patent Literature 1: International Patent Publication No. WO 2014/045481

SUMMARY OF INVENTION

Technical Problem

However, there is a problem that, when noise components are included in the spectral data, an accurate analysis cannot be performed.

The present invention aims to provide a spectroscopic analysis apparatus, a spectroscopic analysis method, and a readable medium capable of appropriately analyzing the sample.

Solution to Problem

A spectroscopic analysis apparatus according to an aspect of the present invention includes: a light source configured to generate light to be incident on a sample including a plurality of substances labeled by a plurality of labeled substances; a spectrometer configured to disperse observed light generated in the sample by the light incident on the sample; a detector configured to detect the observed light dispersed by the spectrometer to output observed spectral data; and a processor configured to analyze the plurality of substances included in the sample based on the observed spectral data output from the detector, the processor analyzing the substances included in the sample from the observed spectral data using a generalized inverse of a matrix having, as elements, reference spectral data set for the plurality of labeled substances and data of a noise component.

A spectroscopic analysis method according to an aspect of the present invention includes: irradiating a sample with light, the sample including a plurality of substances labeled by a plurality of labeled substances; dispersing observed light generated in the sample by the light incident on the sample; detecting the observed light that has been dispersed to output observed spectral data; obtaining a generalized inverse of a matrix having, as elements, a reference spectral data set for the plurality of labeled substances and data of a noise component; and analyzing the substances included in the sample using the generalized inverse and the observed spectral data.

A readable medium according to an aspect of the present invention is a readable medium storing a program for causing a computer to execute a spectroscopic analysis method for analyzing a sample using observed spectral data obtained by spectroscopically measuring light generated in the sample including a labeled substance, in which the spectroscopic analysis method includes: obtaining a generalized inverse of a matrix having, as elements, a reference spectral data set for a plurality of labeled substances and data of a noise component; and analyzing the substances included in the sample using the generalized inverse and the observed spectral data.

Advantageous Effects of Invention

According to the present invention, it is possible to provide a spectroscopic analysis apparatus, a spectroscopic analysis method, and a readable medium capable of appropriately analyzing the sample.

DESCRIPTION OF EMBODIMENTS

With reference to the accompanying drawings, an embodiment of the present invention will be described. The embodiment described below is examples of the present invention and the present invention is not limited to the following embodiment. Throughout the specification and the drawings, the same components are denoted by the same reference symbols.

In this embodiment, a DNA base sequence analysis is performed using a plurality of fluorescent substances having emission wavelengths different from one another. Specifically, DNA is extracted from human cells. DNA fragments are amplified by a polymerase chain reaction (PCR) and are labeled by the fluorescent substances. The fluorescent substances may be, for example, 5-FAM, JOE, NED, and ROX. As a matter of course, the fluorescent substances used for the labeling are not particularly limited. In this example, a plurality of fluorescent substances having peak wavelengths different from one another are used for the labeling. Different bases are labeled by different fluorescent substances.

Different PCR products labeled by fluorescence are supplied to a capillary and are electrophoresed in gel. In a state in which a voltage is applied by electrophoresis, the migration velocity varies depending on the size of the DNA fragment. The migration distance increases as the number of bases decreases. It is therefore possible to separate the DNA fragments by size. When PCR products in the capillary are irradiated with excitation light emitted from a light source, fluorescence is generated from fluorescent substances. The fluorescence generated from the fluorescent substances is spectroscopically measured to obtain observed spectral data. The observed spectral data is obtained for each size of the DNA fragments. By analyzing these observed spectral data, it is possible to quantify DNA of a particular sequence and to execute DNA testing.

While the spectroscopic analysis apparatus is used for DNA testing in this embodiment, the spectroscopic analysis apparatus according to this embodiment is not limited to being applied to the DNA testing. This embodiment can be applied to a spectroscopic analysis apparatus that analyzes the spectrum of the fluorescence generated from the sample that has labeled the substances by a fluorescence probe. It is possible, for example, to analyze nucleic acid, proteins and the like. The spectroscopic analysis apparatus may be used to identify the substances, for example. Further, it is possible to label the substances included in the sample by labeled substances other than the fluorescent substances. The labeled substances may be preferably substances having different light peak wavelengths.

Figure 1:
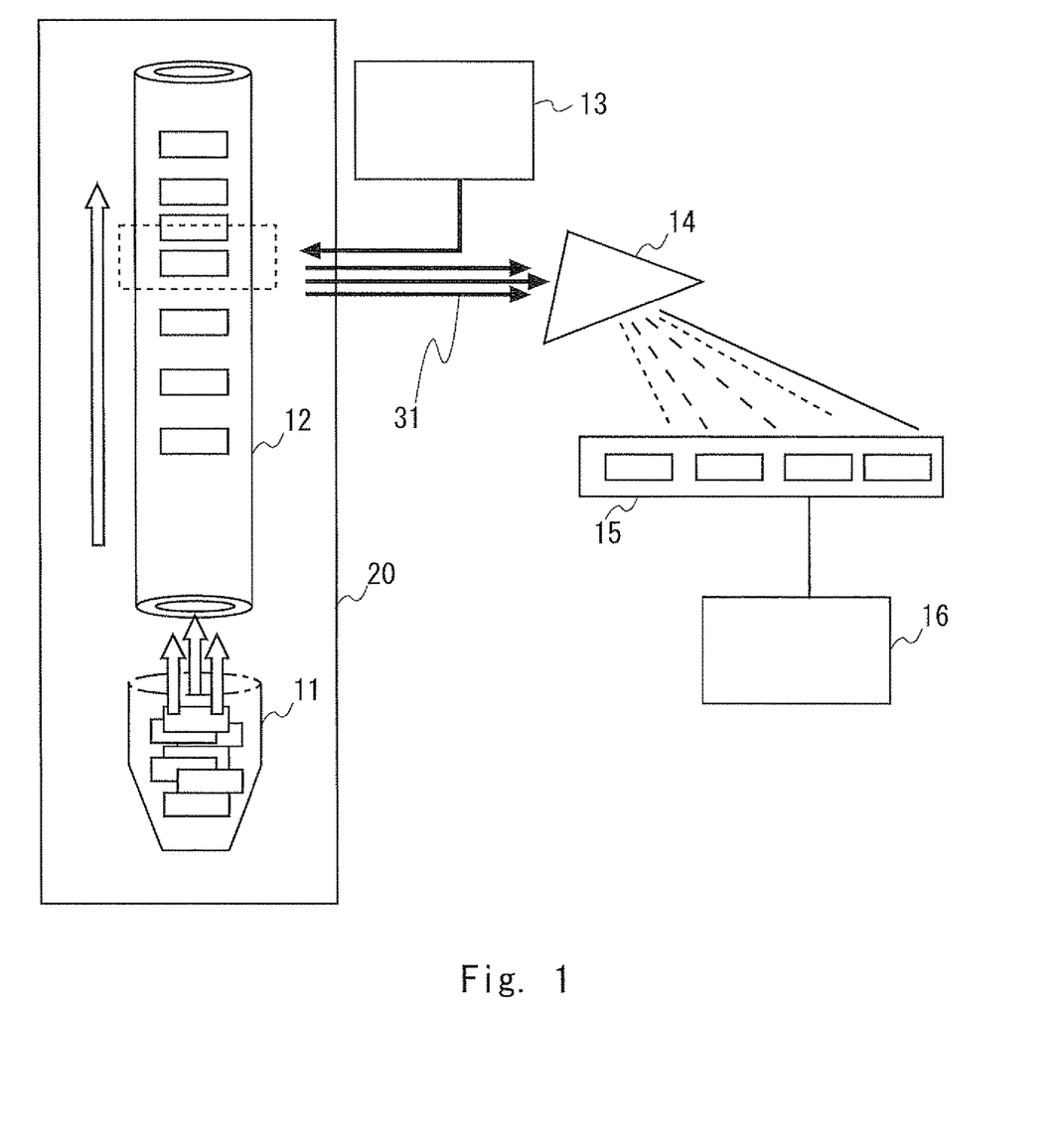
FIG. 1 is a diagram schematically showing a configuration of a spectroscopic analysis apparatus according to an embodiment of the present invention.

With reference to FIG. 1, the spectroscopic analysis apparatus according to the present invention will be described. FIG. 1 is a diagram showing a configuration of the spectroscopic analysis apparatus. The spectroscopic analysis apparatus includes an injection part 11, a capillary 12, a light source 13, a spectrometer 14, a detector 15, a processor 16, a microchip 20, and optical fibers 31. In this example, an analysis is performed using capillary electrophoresis.

PCR products including DNA fragments labeled by fluorescent substances are injected into the injection part 11. In this example, the DNA fragments, which correspond to the sample, are labeled by a plurality of fluorescent substances. For example, fluorescent substances such as 5-FAM, JOE, NED, and ROX are used depending on the base sequence of the DNA fragments. As a matter of course, the type and the number of the fluorescent substances used for the labeling are not particularly limited.

The injection part 11 is communicated with the capillary 12 on the microchip 20. Electrodes (not shown) are arranged on the respective ends of the capillary 12 provided in the microchip 20 and voltages are applied to the electrodes. The capillary 12 and the injection part 11 are filled with an electrophoresis medium such as agarose gel. Accordingly, since the electrophoretic velocity becomes low in accordance with the number of bases of the DNA fragments, the DNA fragments are separated by size.

The light source 13 generates light to be incident on the medium in the capillary. The light source 13 may be, for example, an argon ion laser light source that emits excitation light having a wavelength of 488 nm or 514.5 nm.

The light emitted from the light source 13 is incident on the capillary 12. In this example, 8-lane capillaries 12 are provided in parallel in the microchip 20. When the 8-lane capillaries 12 are irradiated with excitation light, the fluorescent substances that label the DNA fragments in the capillary 12 generate fluorescence. The fluorescence generated by the fluorescent substances becomes observed light.

The fluorescence generated by the fluorescent substances in the sample propagates through the optical fiber 31 and is then input to the spectrometer 14. The spectrometer 14 includes, for example, a prism or diffraction grating, and disperses the fluorescence. In summary, the fluorescence is spatially dispersed in accordance with the wavelength. The fluorescence spatially dispersed by the spectrometer 14 is input to the detector 15. Accordingly, the fluorescence generated by the fluorescent substances becomes observed light observed by the detector.

The detector 15 is, for example, a photodetector such as a CCD sensor, and pixels are arranged along a dispersion direction. Specifically, the detector 15 is a two-dimensional array photodetector in which pixels are arranged along X and Y directions. The X direction and the Y direction are directions perpendicular to each other. The X direction corresponds to a spectroscopic direction and the Y direction corresponds to the direction perpendicular to the spectroscopic direction. Accordingly, fluorescence having wavelengths different from one another is detected for each of the pixels arranged in the dispersion direction (spectroscopic direction).

The detector 15 detects the fluorescence from the fluorescent substances that have labeled the DNA fragments and outputs the detection signal to the processor 16. For example, spectra in a wavelength region of 200 to 800 nm are measured by the spectrometer 14 and the detector 15. The number of pieces of data included in the spectral data varies in accordance with the dispersion performance or the like of the spectrometer 14. As a matter of course, the wavelength region that can be spectroscopically measured by the spectrometer 14 and the detector 15 is not particularly limited. The wavelength region can be appropriately set in accordance with the fluorescent substance used as a label and the excitation light wavelength.

The detector 15 outputs to the processor 16 the light intensity in each wavelength in the wavelength region that can be observed as observed spectral data. The number of pieces of data included in the observed spectral data varies in accordance with the dispersion performance or the like of the spectrometer 14.

The processor 16 is an information processing device such as a personal computer, and performs processing in accordance with a control program. Specifically, the processor 16 stores an analysis program that analyzes the observed spectral data output from the detector 15. The processor 16 executes processing in accordance with the analysis program. The processor 16 analyzes the plurality of substances included in the sample based on the observed spectral data output from the detector 15. The concentrations of the DNA fragments are thus obtained. It is therefore possible to perform DNA testing.

The processing in the processor 16 is one of the characteristics of the spectroscopic analysis method according to this embodiment. The processor 16 analyzes the substances included in the sample from the observed spectral data using a generalized inverse of a matrix having, as elements, reference spectral data set for the plurality of fluorescent substances and data of noise components.

Figure 2:
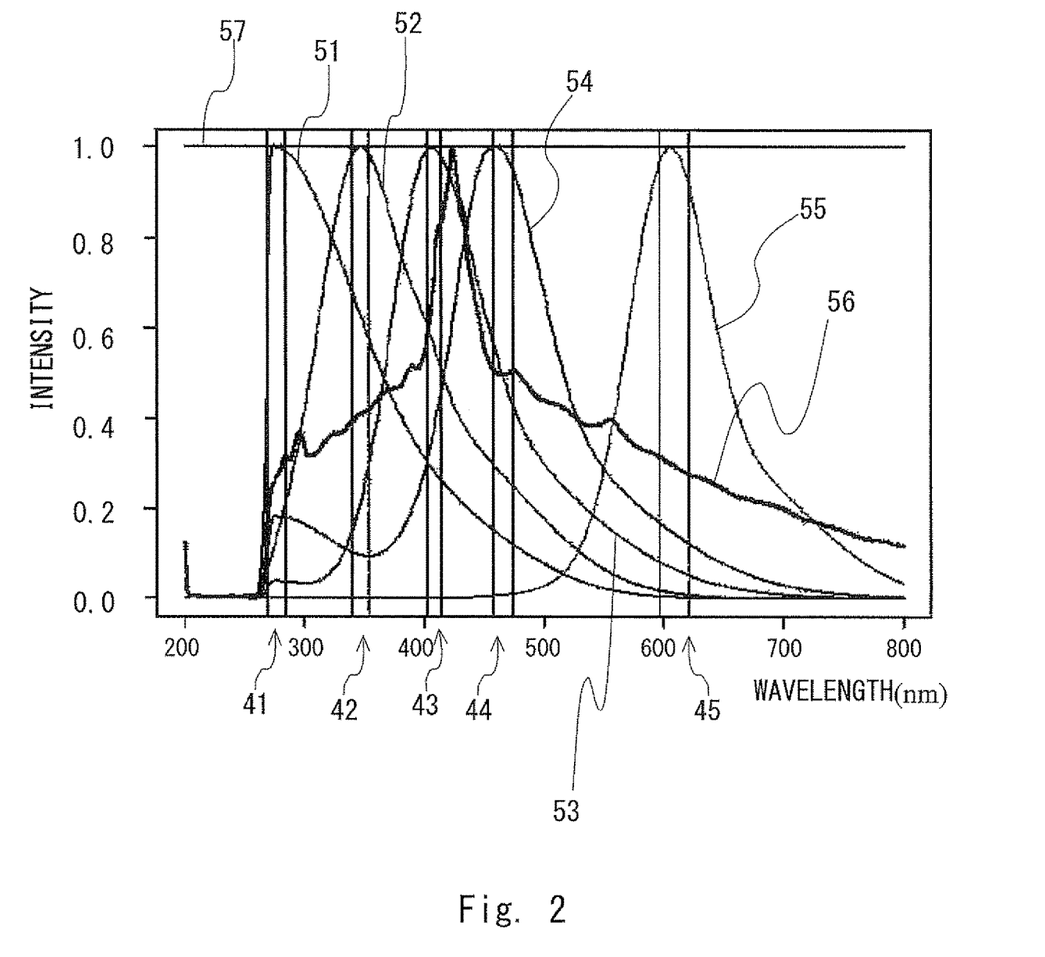
FIG. 2 is a graph showing spectra of fluorescence generated from fluorescent substances that label DNA and spectra of noise components.

In the following description, the processing in the processor 16 will be described. FIG. 2 is a diagram schematically showing the spectra of the fluorescent substances that have labeled the DNA fragments. In this example, a case in which the DNA fragments are labeled using five fluorescent substances will be described.

FIG. 2 shows spectral data of the five fluorescent substances and the noise components. The horizontal axis indicates a wavelength (nm) and the vertical axis indicates a signal intensity. The spectra obtained from the five fluorescent substances are denoted by reference spectra 51-55. That is, the fluorescent spectra when the excitation light is incident on the respective fluorescent substances are denoted by the reference spectra 51-55. That is, the fluorescent spectra of the first fluorescent substance to the fifth fluorescent substance are denoted by the reference spectra 51-55.

Further, a spectrum in a case in which there is no fluorescent substance is denoted by a stray light noise 56. That is, the stray light noise 56 includes the spectral data spectroscopically measured in the state in which there is no fluorescent substance. The reference spectra 51-55 and the stray light noise 56 are normalized in such a way that the peak values (maximum values) thereof become 1. Further, data which has a fixed value irrespective of the wavelength is denoted by an offset noise 57. Since the offset noise 57 is normalized in a similar way, the offset noise 57 has a value of 1, which is a fixed value.

The reference spectra 51-55 of the fluorescent substances are known and vary for each fluorescent substance. That is, the reference spectra have peak wavelengths different from one another. For example, the reference spectrum 51 has its peak at about 280 nm. The reference spectrum 52 has its peak at about 350 nm. The reference spectrum 53 has its peak at about 410 nm. The reference spectrum 54 has its peak at about 570 nm. The reference spectrum 55 has its peak at about 610 nm. Further, the stray light noise 56 has its peak at 420 nm.

The observed spectrum detected by the detector 15 is obtained by overlapping the spectra obtained by multiplying the reference spectra 51-55 shown in FIG. 2 in accordance with the concentrations of the fluorescent substances. Accordingly, by analyzing the observed spectral data to obtain the concentration of each fluorescent substance, the distribution of the concentration of each base can be obtained.

Further, the observed spectrum detected by the detector 15 is obtained by overlapping the stray light noise 56 and the offset noise 57. Further, the level of the stray light noise 56 and that of the offset noise 57 vary with time. Therefore, the concentration of each fluorescent substance included in the sample is obtained after taking into consideration of the stray light noise 56 and the offset noise 57. It is therefore possible to perform analysis more accurately.

In this example, two noises, i.e., the stray light noise 56 and the offset noise 57, are used for the analysis as the noise components. The stray light noise 56 and the offset noise 57 vary with time. For example, the stray light noise 56 is scattered and reflected in a measurement environment and is based on the stray light that is incident on the detector 15. Therefore, the stray light noise 56 varies in accordance with output fluctuations of the light source 13. The offset noise 57 becomes a background noise which has a fixed value irrespective of the wavelength.

The observed spectrum is a total of the fluorescent intensities from the fluorescent substances and the noise components. When, for example, the fluorescent intensities of the five respective fluorescent substances are denoted by F1-F5, the intensity of the stray light noise 56 is denoted by N1, and the intensity of the offset noise is denoted by N2, the intensity I of the observed spectrum becomes the total sum of F1-F5, N1, and N2 as shown in the following (1).

$$I = F1 + F2 + F3 + F4 + F5 + N1 + N2 \quad (1)$$

Ideally, the aforementioned Expression (1) is established in any wavelength. Further, the fluorescent intensities F1-F5 have values in accordance with the concentrations of the respective fluorescent substances. That is, the fluorescent intensities F1-F5 vary depending on the concentrations of the fluorescent substances. The fluorescent intensities F1-F5 can be expressed by the product of the reference spectra 51-55 and the coefficients indicating the concentrations of the respective fluorescent substances. For example, data of the reference spectra 51-55 in the wavelength λ are respectively denoted by A1(λ)-A5(λ) and the coefficients indicating the concentrations of the first fluorescent substance-the fifth fluorescent substance are respectively denoted by x1-x5. Then the fluorescent intensities F1(λ)-F5(λ) in the wavelength λ can be expressed as shown in the following Expression (2).

$$F1(\lambda) = A1(\lambda) \times x1$$

$$F2(\lambda) = A2(\lambda) \times x2$$

$$F3(\lambda) = A3(\lambda) \times x3$$

$$F4(\lambda) = A4(\lambda) \times x4$$

$$F5(\lambda) = A5(\lambda) \times x5 \quad (2)$$

Further, the spectral data of the stray light noise 56 is denoted by A6(λ), the offset noise is denoted by A7(λ), the coefficient indicating the intensity fluctuations of the stray light noise 56 is denoted by x6, and the coefficient indicating the intensity fluctuations of the offset noise is denoted by x7. Further, the data of the offset noise A7(λ) may be, for example, 1, which is a fixed value, irrespective of the wavelength. Accordingly, the intensity N1 of the stray light noise and the intensity N2 of the offset noise can be expressed by the following Expression (3).

$$N1(\lambda) = A6(\lambda) \times x6$$

$$N2(\lambda) = A7(\lambda) \times x7 = 1 \times x7 \quad (3)$$

From the aforementioned (1)-(3), as long as x1-x5 can be obtained, the concentrations of the respective fluorescent substances can be obtained. The processor 16 calculates the generalized inverse of the matrix having, as elements, the light intensity data of the reference spectra 51-55 set for the plurality of labeled substances and the data of noise components. The processor 16 analyzes the DNA fragments included in the sample from the observed spectral data. In the following description, matrix calculations performed by the processor 16 to analyze the sample will be described.

The matrix composed of the light intensity data in each wavelength included in the observed spectral data is denoted by b. When the observed spectral data includes, for example, m (m is an integer larger than 2) pieces of light intensity data, the matrix b has m rows and one column. The elements included in the matrix b are denoted by b1, b2, . . . bm.

Further, the matrix composed of the data included in the reference spectra 51-55 of the five fluorescent substances, the stray light noise 56, and the offset noise 57 is denoted by A. The matrix A has m rows and seven columns. The m pieces of light intensity data included in the reference spectrum 51 are denoted by $A_{11}, A_{21}, A_{31}, \ldots A_{m1}$. The m pieces of light intensity data included in the reference spectrum 52 are denoted by $A_{12}, A_{22}, A_{32}, \ldots A_{m2}$. The m pieces of light intensity data included in the reference spectrum 53 are denoted by $A_{13}, A_{23}, A_{33}, \ldots A_{m3}$, the m pieces of light intensity data included in the reference spectrum 54 are denoted by $A_{14}, A_{24}, A_{34}, \ldots A_{m4}$, and the m pieces of light intensity data included in the reference spectrum 55 are denoted by $A_{15}, A_{25}, A_{35}, \ldots A_{m5}$. The m pieces of data included in the spectral data of the stray light noise 56 are denoted by $A_{16}, A_{26}, A_{36}, \ldots A_{m6}$. The m pieces of data included in the data of the offset noise 57 are denoted by $A_{17}, A_{27}, A_{37}, \ldots A_{m7}$. $A_{17}, A_{27}, A_{37}, \ldots A_{m7}$ all have the same value and may be, for example, 1.

The light intensity data $A_{11}, A_{21}, A_{31}, \ldots A_{m1}$ are the elements of the first row and the light intensity data $A_{12}, A_{22}, A_{32}, \ldots A_{m2}$ are the elements of the second row. Similarly, the data of the reference spectra 53-55 are the elements of the third to fifth rows, respectively. The spectral data $A_{16}, A_{26}, A_{36}, \ldots A_{m6}$ of the stray light noise 56 are the elements of the sixth row, and the data of the offset noise $A_{17}, A_{27}, A_{37}, \ldots A_{m7}$ are the elements of the seventh row. As a matter of course, the positions of the data in the matrix A are not specifically limited. For example, the order of the rows may be changed.

Since the number of fluorescent substances that label the sample is five and the number of noise components is two in this example, the matrix A has m rows and seven columns. However, the number of rows of the matrix A increases depending on the number of fluorescent substances to be used. When, for example, the sample is labeled by two fluorescent substances corresponding to the two bases, the matrix A has m rows and four columns.

Note that the number of pieces of light intensity data of the reference spectra 51-55, the number of pieces of spectral data of the stray light noise, and the number of pieces of data of the offset noise are the same as the number of pieces of light intensity data included in the observed spectrum. That is, the wavelength where the data is present in the observed spectrum, that in the reference spectrum, that in the stray light noise, and that in the offset noise are all the same. As a matter of course, when the number of pieces of data of the reference spectra, that of the stray light noise, and that of the offset noise are different from the number of pieces of data of the observed spectrum, the number of pieces of data may be made the same by complementing data.

Further, the matrix composed of the concentrations of the fluorescent substances included in the sample and the coefficient in accordance with the fluctuations of the noise components is denoted by X. Since the number of fluorescent substances to be used for labeling is five and the number of noise components is two in this example, the matrix X has seven rows and one column. The elements included in the matrix X are denoted by x1-x7. The processor 16 executes processing for obtaining the matrix X.

In each wavelength, the following Expression (4) is established.

$$b_j = A_{j1} \times x_1 + A_{j2} \times x_2 + A_{j3} \times x_3 + A_{j4} \times x_4 + A_{j5} \times x5 + A_{j6} \times x_6 + A_{j7} \times x_7 \quad (4)$$

Note that j is any integer from 1 to m. That is, from the product of the coefficient of the concentration of the fluorescent substance used for labeling and the light intensity data of the reference spectrum in one wavelength, and the noise components and the coefficients indicating the fluctuations of the noise components, the light intensity data of the observed spectrum in this wavelength is calculated. Since Expression (4) is established for any desired wavelength, when Expression (4) is expressed using the matrix A, the matrix b, and the matrix X, Expression (5) in FIG. 3 can be obtained.

Figure 3:
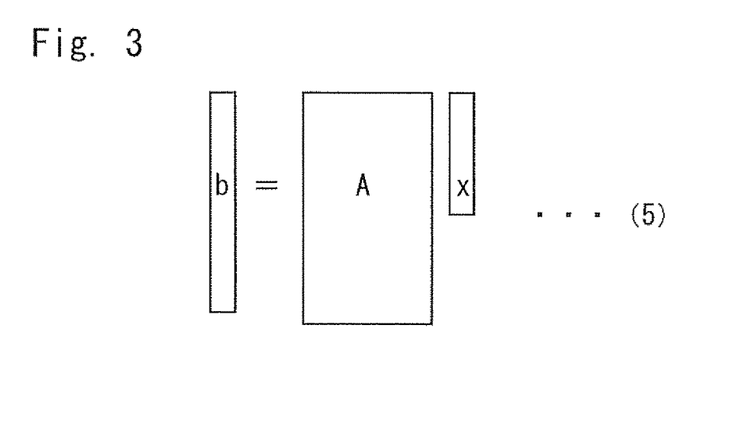
FIG. 3 is a diagram showing a matrix calculation expression for performing DNA analysis.
Figure 4:
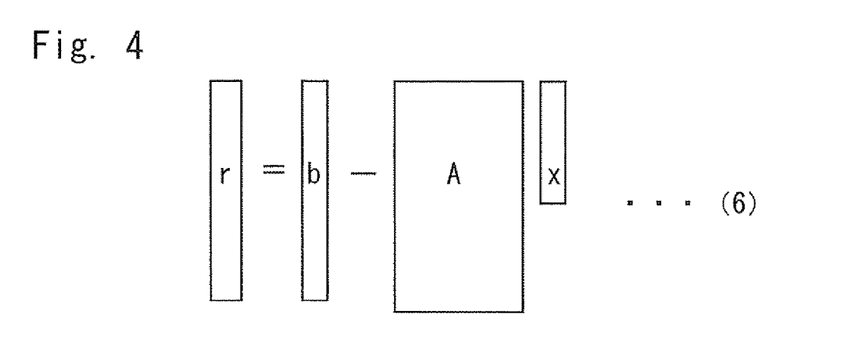
FIG. 4 is a diagram showing a matrix calculation expression for performing the DNA analysis.

In an ideal measurement, Expression (5) in FIG. 3 is established. While there are seven elements $x_1, x_2$ of the matrix X to be obtained, the number of conditional expressions is m. Since m is larger than 7, the number of conditions is too large. In order to solve this problem, the approximate solution that minimizes the error r shown in Expression (6) in FIG. 4 is obtained. This approximate solution is the least squares problem that minimizes |r|.

Since A is not a square matrix, there is no inverse matrix. It is also possible, however, to calculate a generalized inverse (or generalized inverse matrix). By using the generalized inverse, the matrix X can be calculated from Expression (6) shown in FIG. 3. In summary, the processor 16 obtains the least squares optimal solution by the generalized inverse.

Figure 5:
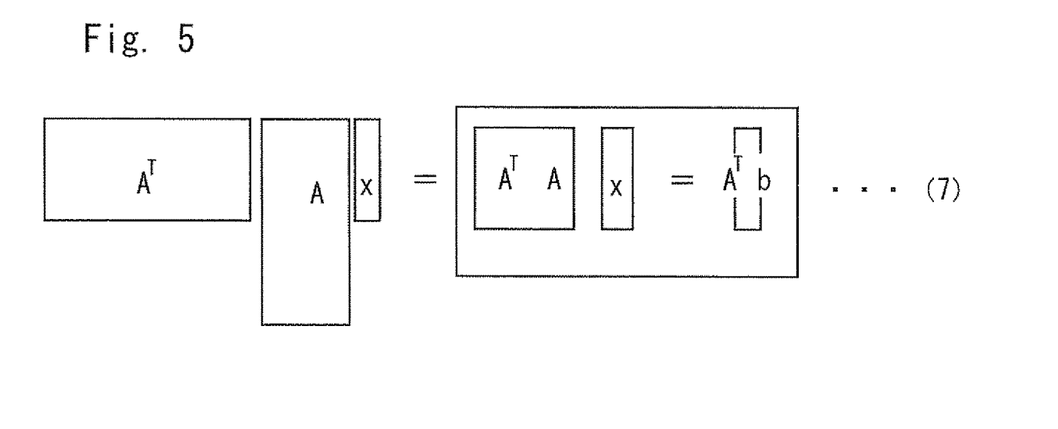
FIG. 5 is a diagram showing a matrix calculation expression for performing the DNA analysis.

It is assumed that the matrix $A^T$ has seven rows and m columns. As shown in Expression (7) in FIG. 5, $A^T A$ is a square matrix (in this example, seven rows and seven columns), whereby it is possible to obtain the inverse matrix. When the inverse matrix of $A^T A$ is $(A^T A)^{-1}$, the matrix X can be calculated by the following Expression (8) from Expression (7) in FIG. 5.

$$X = (A^T A)^{-1} A^T b \quad (8)$$

Figure 6:
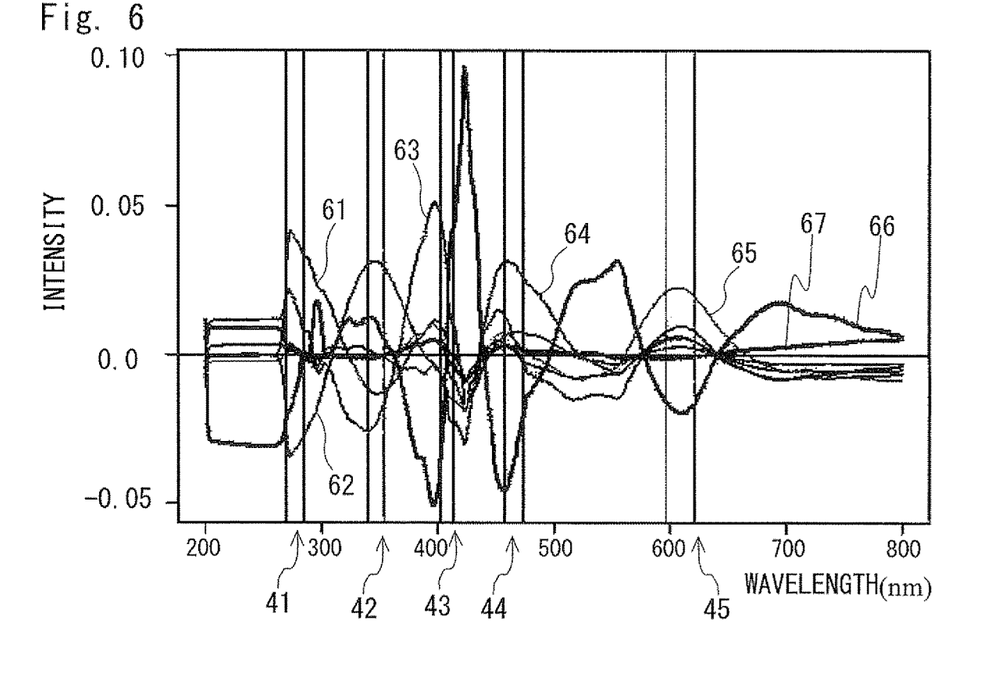
FIG. 6 is a diagram showing data of a generalized inverse of a matrix A.

Expression (8) means obtaining the least square solution that minimizes the error r shown in Expression (6) in FIG. 4. Since the matrix A is composed of the known reference spectra 51-55, the stray light noise 56, and the offset noise 57, it is possible to unambiguously calculate $(A^T A)^{-1} A^T$. FIG. 6 shows the generalized inverse of the matrix A having, as an element, the data shown in FIG. 2.

It is possible to calculate the matrix X by multiplying the matrix b of the observed spectrum by $(A^T A)^{-1} A^T$. It is therefore possible to obtain the concentrations of the fluorescent substances. When $C = (A^T A)^{-1} A^T$, for example, C is the generalized inverse. The product of the generalized inverse C of A and the matrix b is then obtained. The elements of the generalized inverse $(A^T A)^{-1} A^T$ are generalized inverse data 61-67 shown in FIG. 6. In summary, the matrix has seven rows and m columns, the first row to the seventh row being the generalized inverse data 61-67, respectively. By calculating the product of the matrix of the observed spectral data and the generalized inverse, it is possible to calculate the rate of the plurality of labeled substances included in the sample. The data of the generalized inverse can be obtained in advance from the data of the reference spectrum, the stray light noise, and the offset noise.

It is therefore possible to calculate the concentrations of the plurality of fluorescent substances used for the labeling in a simple way. In the matrix operation using the generalized inverse, the data of noise components is added as an element of the matrix. According to this configuration, even in a measurement environment in which there are noise components, the concentrations of the fluorescent substances can be appropriately obtained. Even when the excitation light output from the light source fluctuates or the electrical offset noise fluctuates, for example, the concentrations of the fluorescent substances can be appropriately obtained. When, in particular, the intensities of the noise components fluctuate, it becomes difficult to remove only the noise components from the observed spectrum. However, in the matrix operation described in this embodiment, the noise components can be easily removed. It is therefore possible to calculate the concentrations more accurately.

While the case in which the noise components include the stray light noise 56 and the offset noise 57 has been described in the aforementioned description, only one of them may be incorporated into the matrix operation. When the stray light noise 56 that is fluctuated in accordance with the wavelength is negligible in the observed spectral data, only the offset noise can be used. Further, when the offset noise 57 that is fixed irrespective of the wavelength is negligible in the observed spectral data, only the stray light noise 56 can be used.

Further, since windows 41-45 are not set unlike in the case shown in FIG. 2, it is possible to calculate the concentrations more accurately. For example, by setting the windows 41-45, light intensity data of the observed spectrum outside the windows 41-45 is not used any more. In summary, the number of pieces of light intensity data to obtain the concentrations of the fluorescent substances becomes small, which causes degradation of the accuracy of the calculation. Meanwhile, in this embodiment, a larger number of pieces of light intensity data included in the observed spectrum can be used, whereby it is possible to decrease the noise and to improve the measurement accuracy. It is therefore possible to obtain the concentrations accurately and to perform a more appropriate analysis.

As described above, the processor 16 analyzes the plurality of substances included in the sample based on the observed spectral data output from the detector 15. Accordingly, the processor 16 obtains the generalized inverse of the matrix having, as elements, the reference spectral data set for the plurality of labeled substances that label the plurality of substances and the data of the noise components. The processor 16 analyzes the substances included in the sample using the observed spectral data and the generalized inverse. If the generalized inverse of the matrix of the reference spectra and the noise components is calculated in advance, the processing can be executed in a shorter period of time. That is, the generalized inverse may be acquired by reading out the generalized inverse stored in a storage unit such as a memory in advance. As a matter of course, the generalized inverse may be obtained by calculating the generalized inverse using the data of stray light noise that has been measured.

It is therefore possible to perform an analysis using a larger number of observed spectral data. It is therefore possible to appropriately analyze the sample based on the spectrum of the fluorescence and to perform DNA testing with a small measurement error.

As described above, by electrophoresing the PCR amplified sample, the DNA fragments are separated by size. The DNA fragments in the capillary are irradiated with light to detect the observed spectrum in each size of the DNA fragments. The plurality of observed spectra are subjected to the above processing to calculate the concentration of each base. The distribution of the concentration of the base is obtained for each size of the DNA fragments. The DNA testing is carried out in accordance with the base sequence of the DNA fragment. It is therefore possible to perform DNA testing with higher accuracy.

Other Embodiments

Figure 7:
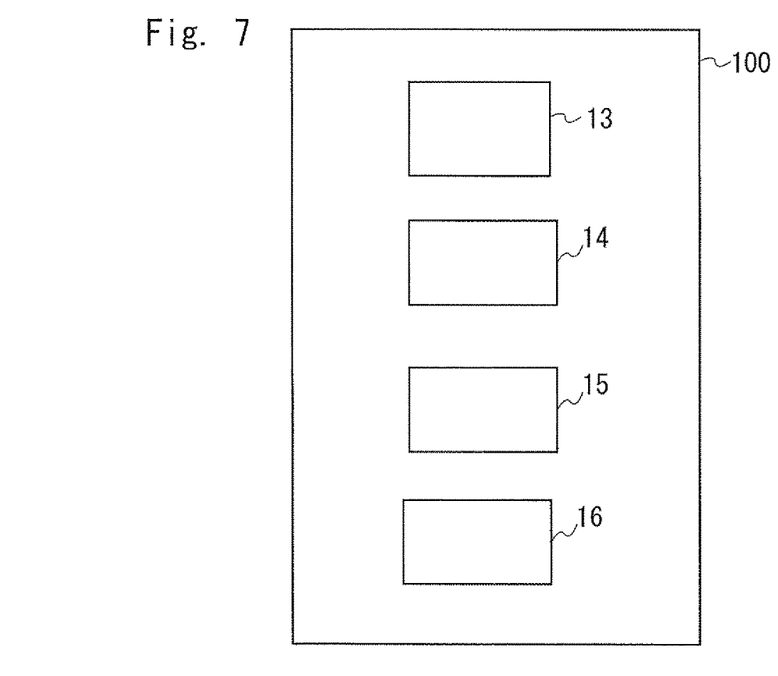
FIG. 7 is a block diagram showing a configuration of a spectroscopic analysis apparatus according to another embodiment.

With reference to FIG. 7, a spectroscopic analysis apparatus 100 according to another embodiment will be described. FIG. 7 is a block diagram showing a configuration of the spectroscopic analysis apparatus 100. The spectroscopic analysis apparatus 100 includes a light source configured to generate light to be incident on a sample comprising a plurality of substances labeled by a plurality of labeled substances; a spectrometer configured to disperse observed light generated in the sample by the light incident on the sample; a detector configured to detect the observed light dispersed by the spectrometer to output observed spectral data; and a processor configured to analyze the plurality of substances included in the sample based on the observed spectral data output from the detector, the processor analyzing the substances included in the sample from the observed spectral data using a generalized inverse of a matrix having, as elements, reference spectral data set for the plurality of labeled substances and data of noise components. According to this configuration, it is possible to analyze the sample appropriately.

The control for analyzing the above sample may be executed by a computer program. The control program described above can be stored and provided to a computer using any type of non-transitory computer readable media. Non-transitory computer readable media include any type of tangible storage media. Examples of non-transitory computer readable media include magnetic storage media (such as flexible disks, magnetic tapes, hard disk drives, etc.), optical magnetic storage media (e.g. magneto-optical disks), CD-ROM (Read Only Memory), CD-R, CD-R/W, and semiconductor memories (such as mask ROM, PROM (Programmable ROM), EPROM (Erasable PROM), flash ROM, RAM (Random Access Memory), etc.). The program may be provided to a computer using any type of transitory computer readable media. Examples of transitory computer readable media include electric signals, optical signals, and electromagnetic waves. Transitory computer readable media can provide the program to a computer via a wired communication line (e.g. electric wires, and optical fibers) or a wireless communication line.

Further, the embodiments of the present invention include not only the case in which the functions of the above embodiments are achieved by the computer executing the program that achieves the functions of the above embodiments but also a case in which this program achieves the functions of the above embodiments in collaboration with an application software or an operating system (OS) operated on the computer.

While the present invention has been described with reference to the embodiments, the present invention is not limited to the above embodiments. Various changes that can be understood by those skilled in the art may be made on the configuration and the details of the present invention within the scope of the present invention.

This application is based upon and claims the benefit of priority from Japanese Patent Application No. 2015-71618, filed on Mar. 31, 2015, the disclosure of which is incorporated herein in its entirety by reference.

REFERENCE SIGNS LIST

11 INJECTION PART
12 CAPILLARY
13 LIGHT SOURCE
14 SPECTROMETER
15 DETECTOR
16 PROCESSOR
20 MICROCHIP
31 OPTICAL FIBER
41-44 WINDOW 51-55 REFERENCE SPECTRUM
56 STRAY LIGHT NOISE
57 OFFSET NOISE
61-67 GENERALIZED INVERSE DATA

The invention claimed is:

1. A spectroscopic analysis apparatus comprising:
a light source configured to generate light to be incident on a sample comprising a plurality of substances labeled by a plurality of labeled substances;
a spectrometer configured to disperse observed light generated in the sample by the light incident on the sample;
a detector configured to detect the observed light dispersed by the spectrometer to output observed spectral data; and
a processor configured to analyze the plurality of substances included in the sample based on the observed spectral data output from the detector, the processor analyzing the substances included in the sample from the observed spectral data using a generalized inverse of a matrix having, as elements, reference spectral data set for the plurality of labeled substances and data of a noise component,
wherein the data of the noise component comprises data of stray light noise spectroscopically measured in the absence of the labeled substance,
wherein a level of the stray light noise varies with time,
wherein the stray light noise fluctuates in accordance with wavelength,
wherein, if a number of pieces of the reference spectral data and a number of pieces of data of the noise component are different from a number of pieces of the observed spectrum data, then the processor performs data complementation on at least one of the reference spectrum data, the data of the noise component and the observation spectrum data so that the number of pieces of the reference spectrum data, the number of pieces of data of the noise component and the number of pieces of the observed spectrum data, coincide with each other, and
wherein the processor sets the data of the noise component to 0 in the matrix when the data of the noise component is negligible in the observed spectral data.

2. The spectroscopic analysis apparatus according to claim 1, wherein the data of the noise component comprises data of offset noise, the element of the matrix of the data of the offset noise being a fixed value irrespective of a wavelength.

3. The spectroscopic analysis apparatus according to claim 1, comprising calculating the product of the matrix of the observed spectral data and the generated inverse to calculate a rate of the plurality of labeled substances included in the sample.

4. The spectroscopic analysis apparatus according to claim 1, wherein the plurality of substances included in the sample are DNA fragments,
wherein the sample is PCR amplified and subjected to electrophoresis to separate the DNA fragments by size, and
wherein DNA testing is performed in accordance with a base sequence of the DNA fragments separated by size.

5. A spectroscopic analysis method comprising:
irradiating a sample with light, the sample comprising a plurality of substances labeled by a plurality of labeled substances;
dispersing observed light generated in the sample by the light incident on the sample;
detecting the observed light that has been dispersed to output observed spectral data;
obtaining a generalized inverse of a matrix having, as elements, a reference spectral data set for the plurality of labeled substances and data of a noise component; and
analyzing the substances included in the sample using the generalized inverse and the observed spectral data,
wherein the data of the noise component comprises data of stray light noise spectroscopically measured in the absence of the labeled substance,
wherein a level of the stray light noise varies with time,
wherein the stray light noise fluctuates in accordance with wavelength,
wherein, if a number of pieces of the reference spectral data and a number of pieces of data of the noise component are different from a number of pieces of the observed spectrum data, then data complementation is performed on at least one of the reference spectrum data, the data of the noise component and the observation spectrum data so that the number of pieces of the reference spectrum data, the number of pieces of data of the noise component and the number of pieces of the observed spectrum data, coincide with each other, and
wherein the data of the noise component is set to 0 in the matrix when the data of the noise component is negligible in the observed spectral data.

6. The spectroscopic analysis method according to claim 5, wherein the data of the noise component comprises data of offset noise, the element of the matrix of the data of the offset noise being a fixed value irrespective of a wavelength.

7. The spectroscopic analysis method according to claim 5, comprising calculating the product of the matrix of the observed spectral data and the generated inverse to calculate a rate of the plurality of labeled substances included in the sample.

8. The spectroscopic analysis method according to claim 5, wherein the plurality of substances included in the sample are DNA fragments,
wherein the sample is PCR amplified and subjected to electrophoresis to separate the DNA fragments by size, and
wherein DNA testing is performed in accordance with a base sequence of the DNA fragments separated by size.

9. A non-transitory computer readable medium storing a program for causing a computer to execute a spectroscopic analysis method for analyzing a sample using observed spectral data obtained by spectroscopically measuring light generated in the sample comprising a labeled substance, wherein the spectroscopic analysis method comprises:
obtaining a generalized inverse of a matrix having, as elements, a reference spectral data set for a plurality of labeled substances and data of a noise component; and
analyzing the substances included in the sample using the generalized inverse and the observed spectral data,
wherein the data of the noise component comprises data of stray light noise spectroscopically measured in the absence of the labeled substance,
wherein a level of the stray light noise varies with time,
wherein the stray light noise fluctuates in accordance with wavelength,
wherein, if a number of pieces of the reference spectral data and a number of pieces of data of the noise component are different from a number of pieces of the observed spectrum data, then data complementation is performed on at least one of the reference spectrum data, the data of the noise component and the observation spectrum data so that the number of pieces of the reference spectrum data, the number of pieces of data of the noise component and the number of pieces of the observed spectrum data, coincide with each other, and wherein the data of the noise component is set to 0 in the matrix when the data of the noise component is negligible in the observed spectral data.

10. The non-transitory computer readable medium according to claim 9, wherein the data of the noise component comprises data of offset noise, the element of the matrix of the data of the offset noise being a fixed value irrespective of a wavelength.

11. The non-transitory computer readable medium according to claim 9, comprising calculating the product of the matrix of the observed spectral data and the generated inverse to calculate a rate of the plurality of labeled substances included in the sample.

12. The non-transitory computer readable medium according to claim 9, wherein the plurality of substances included in the sample are DNA fragments, wherein the sample is PCR amplified and subjected to electrophoresis to separate the DNA fragments by size, and wherein DNA testing is performed in accordance with a base sequence of the DNA fragments separated by size.

* * * * *